(12) United States Patent
Augustine et al.

(10) Patent No.: US 7,339,377 B2
(45) Date of Patent: Mar. 4, 2008

(54) METHODS AND DEVICES FOR ANALYSIS OF SEALED CONTAINERS

(75) Inventors: Matthew P. Augustine, Davis, CA (US); April J. Weekley, Orondo, WA (US); Paul Bruins, Winters, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 11/373,052

(22) Filed: Mar. 10, 2006

(65) Prior Publication Data

US 2007/0001673 A1    Jan. 4, 2007

Related U.S. Application Data

(63) Continuation of application No. 11/016,305, filed on Dec. 16, 2004, now Pat. No. 7,012,427, which is a continuation of application No. 10/622,008, filed on Jul. 16, 2003, now Pat. No. 6,911,822.

(60) Provisional application No. 60/465,644, filed on Apr. 25, 2003, provisional application No. 60/396,644, filed on Jul. 17, 2002.

(51) Int. Cl.
G01V 3/00 (2006.01)
(52) U.S. Cl. ...................... 324/321; 324/312
(58) Field of Classification Search ............... 324/321, 324/312, 309, 307
See application file for complete search history.

(56) References Cited

U.S. PATENT DOCUMENTS

| | | | |
|---|---|---|---|
| 3,975,675 A * | 8/1976 | Dunand et al. | 324/312 |
| 4,045,723 A * | 8/1977 | Ernst | 324/309 |
| 4,550,082 A | 10/1985 | Martin et al. | |
| 5,270,650 A | 12/1993 | Schenz et al. | |
| 5,530,353 A | 6/1996 | Blanz | |
| 5,811,305 A | 9/1998 | Ono et al. | |
| 6,333,629 B1 | 12/2001 | Pykett et al. | |
| 6,462,546 B1 | 10/2002 | Schmalbein et al. | |
| 6,806,090 B1 | 10/2004 | Hylands et al. | |

OTHER PUBLICATIONS

Drysdale and Fleet "Acetic Acid Bacteria in Winemaking: A Review" Am. J. Enol. Vitic. 39:143-154 (1988).

Castiñeira et al. "Simultaneous Determination of Organic Acids in Wine Samples by Capillary Electrophoresis and UV Detection: Optimization with Five Different Background Electrolytes" J. High Resol. Chromatogr. 23:647-652 (2000).

Guillou and Reniero "Magnetic Resonance Sniffs Out Bad Wine" Physics World 11:22-23 (1998).

Hayes et al. "An Efficient, Highly Homogeneous Radiofrequency Coil for Whole-Body NMR Imaging at 1.5 T" J. Magn. Reson. 63:622-628 (1985).

Schindler et al. "A Rapid Automated Method for Wine Analysis Based Upon Sequential Injection (SI)-FTIR spectroscopy" Fresenius 362:130-136 (1998).

(Continued)

Primary Examiner—Louis M. Arana
(74) Attorney, Agent, or Firm—Quine Intellectual Property Law Group, P.C.

(57) ABSTRACT

This invention provides methods, NMR probes, and NMR systems for the analysis of the contents of sealed food and beverage containers and the like.

26 Claims, 10 Drawing Sheets

OTHER PUBLICATIONS

Vonach et al. "High Performance Liquid Chromatography with Real-Time Fourier-Transform Infrared Detection for the Determination of Carbohydrates, Alcohols and Organic Acids in Wines" J. Chromatogr. A. 824:159-167 (1998).

Košir et al. "Wine Analysis by 1D and 2D NMR Spectroscopy" Analysis 26:97-101 (1998).

Millet and Lonvaud-Funel "The Viable but Non-Culturable State of Wine Micro-Organisms During Storage" Lt. Appl. Microbiol. 30:136-141 (2000).

Ribéreau-Gayon "New Developments in Wine Microbiology" Am. J. Enol. Vitic. 36:1-10 (1985).

Weekley et al. "Using NMR to Study Full Intact Wine Bottles" J. Magn. Reson. 161:91-98 (2003).

* cited by examiner

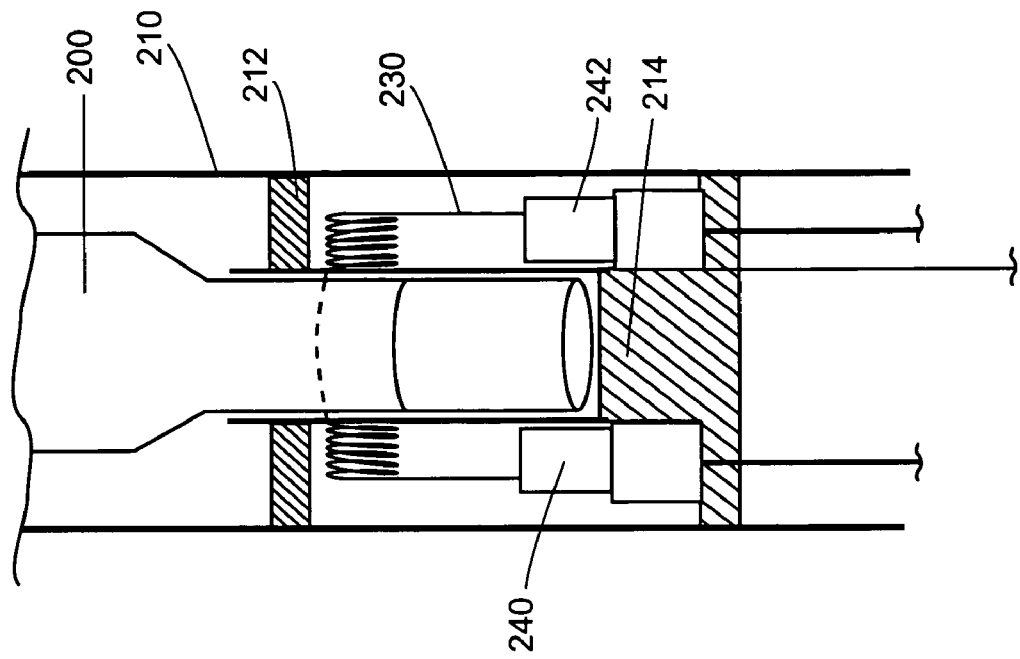
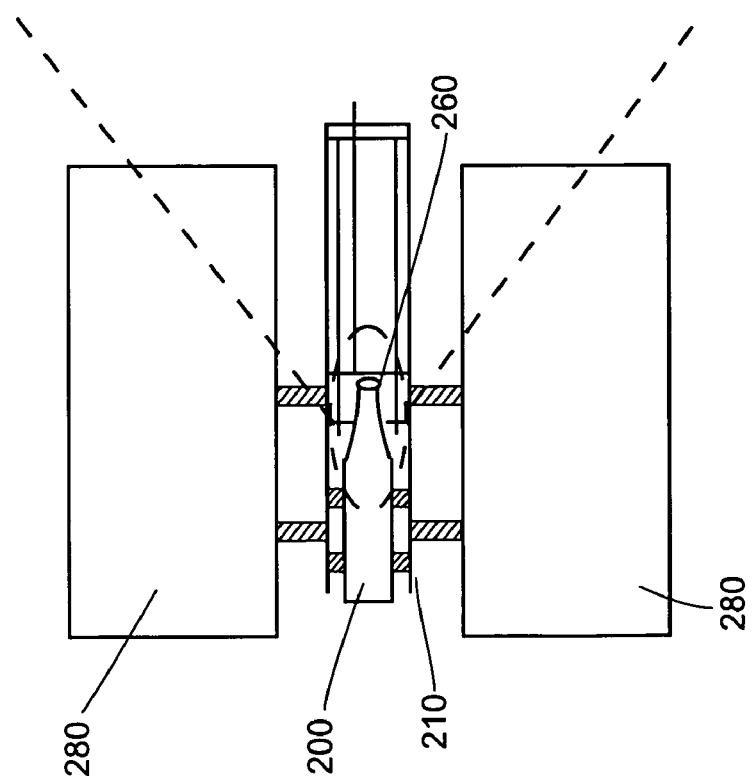
Fig. 3B
Fig. 3A

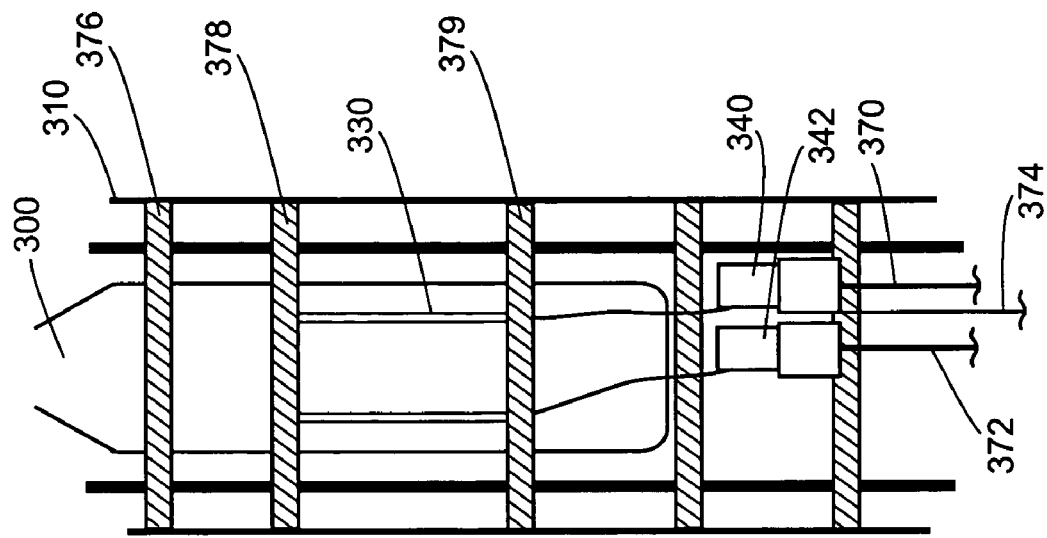
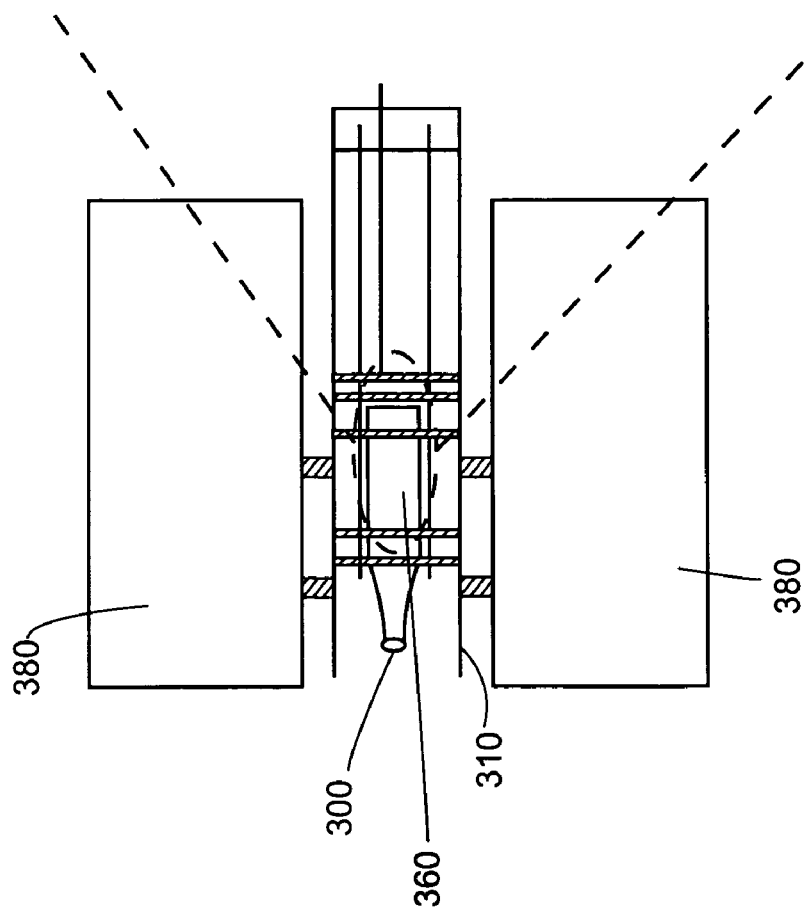
Fig. 4A
Fig. 4B

METHODS AND DEVICES FOR ANALYSIS OF SEALED CONTAINERS

CROSS-REFERENCE TO RELATED APPLICATIONS

This application is a continuation of U.S. patent application Ser. No. 11/016,305 filed Dec. 16, 2004 now U.S. Pat. No. 7,012,427, which is a continuation of U.S. patent application U.S. Ser. No. 10/622,008 filed Jul. 16, 2003, now U.S. Pat. No. 6,911,822, which claims priority to and benefit of U.S. application 60/396,644, filed Jul. 17, 2002 and 60/465,644, filed Apr. 25, 2003, the full disclosures of which are incorporated herein by reference.

FIELD OF THE INVENTION

This invention relates to methods and devices for analyzing sealed food and beverage containers, and particularly sealed wine bottles, by NMR spectroscopy.

BACKGROUND OF THE INVENTION

Wine is the product of the growth and metabolism of yeasts and bacteria in grape must. It is well known that many of these and other bacteria survive all of the steps of wine making from the mature grape through vinification to bottle corking (Ribéreau-Gayon (1985) "New developments in wine microbiology" *Am. J. Enol. Vitic.* 36:1-10). One class of organisms of interest is *Acetobacter*, a bacteria responsible for oxidizing ethyl alcohol into vinegar or acetic acid (Drysdale and Fleet (1988) "Acetic acid bacteria in winemaking: a review" *Am. J. Enol. Vitic.* 39:143-154; Millet and Lonvaud-Funel (2000) "The viable but non-culturable state of wine micro-organisms during storage" *Lt. Appl. Microbiol.* 30:136-141). Although present in most wines, *Acetobacter* does not typically generate enough acetic acid to spoil wine during bottle storage due to a lack of oxygen. As long as the wine is stored in an anaerobic environment, conditions ensured by quality corking, acceptably low quantities of acetic acid (e.g., below sensory levels) are produced and the quality of the wine is preserved. Unfortunately, the sealing performance of wine corks can degrade with age, and the long term behavior of low quality natural corks and synthetic stoppers is not well documented. One consequence of a leaky cork is the admission of oxygen to wine, a triggering of *Acetobacter* function, and the production of acetic acid. Furthermore, the admission of oxygen into the bottle in the presence of heat can lead to oxidation of ethanol into aldehydes. These processes lead to changes in odor and flavor, and therefore spoilage, of fine wines.

Current methods for identifying acetic acid in wine are very sensitive, detecting roughly 50 μg/L acetic acid, even though the accepted spoilage limit of acetic acid in wine is 1.4 g/L (see, for example, Vonach et al. (1998) "High performance liquid chromatography with real-time Fourier-transform infrared detection for the determination of carbohydrates, alcohols and organic acids in wines" *J. Chromatogr. A.* 824:159-167; Castinñeira et al. (2000) "Simultaneous determination of organic acids in wine samples by capillary electrophoresis and UV detection: optimization with five different background electrolytes" *J. High Resol. Chromatogr.* 23:647-652; Schindler et al. (1998) "A rapid automated method for wine analysis based upon sequential injection (SI)-FTIR spectroscopy" *Fresenius J. Anal. Chem.* 362:130-136; and Margalith (1981) in *Flavour Microbiology*, pp. 167-168, Charles Thomas Publishers, Springfield, Ill.). In addition, nuclear magnetic resonance (NMR) spectroscopy has been employed for wine fingerprinting studies and trace amino acid and organic molecule detection in wine (Guillou and Reniero (1998) "Magnetic resonance sniffs out bad wine" *Physics World* 11:22-23; and Košir et al. (1998) "Wine analysis by 1D and 2D NMR spectroscopy" *Analysis* 26:97-101). However, all published NMR studies of wine involve removal and analysis of small volume samples of wine (e.g., less then 1 mL) to accomplish these measurements. As such, all of the current strategies for contaminant (e.g., acetic acid) detection require the bottle to be violated, a process that destroys the cork, seal, and label, severely devaluing both the wine and bottle. The present invention overcomes these and other problems by providing methods and devices for the detection of contaminants in wine bottles by NMR spectroscopy. These methods are equally applicable to other sealed consumables containers for which contamination, degradation, or other changes in product flavor or quality is a concern.

SUMMARY OF THE INVENTION

The present invention provides methods and devices for the analysis of sealed consumable containers by NMR spectroscopy. The high static and radiofrequency (rf) magnetic fields used in the NMR experiment in no way affect the quality of the food or beverage examined via the methods provided herein.

In some embodiments, the present invention provides non-invasive, non-destructive analytical methods for determining the level of wine acetification. As such, the methods and devices of the present invention can be routinely used in the evaluation of the quality of fine wines and in the study of wine cork aging. Furthermore, these methods of intact bottle analysis are not limited to the determination of acetic acid spoilage and content in wines, but can be extended to the study of other wine molecular components (e.g., aldehydes and flavenoids), as well as to components and/or contaminants in other types of sealed consumables.

Accordingly, the present invention provides methods for analyzing one or more contents of a sealed consumables container. The methods include, but are not limited to, the steps of providing an NMR spectrometer and an NMR probe configured to accept a portion of the sealed consumables container; positioning the portion of the sealed consumables container within a data collection region of the NMR probe; establishing a homogeneous static magnetic field across the data collection region; collecting an NMR spectrum; and analyzing one or more peaks in the NMR spectrum, thereby analyzing one or more contents of the sealed consumables container.

Any food or beverage having components that generate one or more NMR peaks can be assessed using the methods and devices of the present invention. Thus, a variety of food or beverage containers having, for example, nonalcoholic beverages, alcoholic beverages, beer, vinegar or olive oil stored therein, can be analyzed using the methods of the present invention. In a preferred embodiment, the sealed consumables container is a bottle of wine.

The methods of the present invention can be used in a qualitative or quantitative manner, e.g., either the presence of a selected component or the concentration of the selected component is determined. For example, in the analysis of wine, exemplary selected components include, but are not limited to, acetic acid, aldehydes, flavenoids, and amino acids.

The methods of the present invention include the step of positioning the portion of the consumables container within a data collection region of the NMR probe. For example, either the neck of the container or a portion of the body of the container can be placed within the data collection region of the NMR probe. The homogeneous static magnetic field is then established across the data collection region by, for example, adjusting the one or more shim coils in the probe. Preferably, establishing the homogeneous field allows for resolution of chemical shift difference between selected NMR spectra peaks a minimum distance apart. In certain embodiments of the present invention involving $^1$H NMR spectroscopy, the resolution will preferably allow for distinguishing peaks that are about 1 ppm apart. Optionally, the NMR peaks generated by the selected components are integrated, thereby analyzing a quantity of the selected component.

The present invention also provides NMR probes configured to position a portion of a sealed consumables container within an NMR spectrometer. The NMR probes used in the present invention can be any of a number of detection probes, including, but not limited to, a $^1$H probe, a $^2$H probe, a $^{13}$C probe, a $^{17}$O probe, or a combination thereof. The NMR probe components include a body structure having a cavity adapted for receiving a portion of the sealed consumables container (e.g., a neck of a bottle, or a body of the container). The cavity is typically disposed in the body structure (either at a first end, or in a middle portion), such that a first rf coil attached to the body structure is positioned proximal to the cavity and the portion of the sealed container. In one embodiment of the probes of the present invention, the first rf coil comprises a split solenoid coil, in which the coil portions are positioned to either side of the data collection region of the probe. In an alternate embodiment, the first rf coil is a birdcage-style coil surrounding the data collection region of the probe.

In some embodiments of the present invention, the first rf coil is used for both transmitting and receiving rf pulses. Optionally, the probe includes a second rf coil positioned distal to the first rf coil. The second rf coils can be, for example, configured for measurement of one or more signals from a calibration sample. Alternatively, the second rf coil is configured for selective excitation of a heteronucleus, such as $^{13}$C, $^{17}$O, $^2$H, $^{23}$Na, $^{27}$Al, $^{199}$Hg, or $^{207}$Pb.

The probes of the present invention further include a tuning capacitor coupled at a first position to the rf coil, and coupled at a second position to a length of coaxial cable configured for connection to the NMR spectrometer. The tuning capacitor can include, but is not limited to, one or more non-magnetic zero-to-ten (0-10) picofarad high power rf capacitors.

Optionally, the probe also includes additional components useful for NMR analyses, such as electronic components for generating magnetic field gradients, a calibration fluid sample tube; and a fluid jacket for modulating the probe temperature, to name a few.

Systems for analyzing contents of a sealed consumables container are also provided by the present invention. The system components include, but are not limited to, the NMR probe configured to position a portion of a sealed consumables container within an NMR spectrometer; an NMR spectrometer having a bore proximal to a magnet and configured to receive the NMR probe, an amplifier coupled to the NMR probe via co-axial cable; and a receiver system having a preamplifier and a detector. Optionally, the system further includes a pulse programmer.

Optionally, the NMR probe of the system is a single resonance probe selected from the group consisting of a $^1$H probe, a $^2$H probe, a $^{13}$C probe, an $^{17}$O probe, a $^{23}$Na probe, an $^{27}$Al probe, a $^{199}$Hg probe, and a $^{207}$Pb probe. In one embodiment, the NMR probe employs a first rf coil used for both transmitting and receiving rf pulses. In another aspect, the NMR probe further comprises a second rf coil configured, for example, for measurement of one or more signals from a calibration sample.

The NMR probe is configured to accept the sealed consumables container and position a portion of the container (e.g., the neck of a bottle, or the body of the container) within the magnetic field of the spectrometer. Typically, the spectrometer comprises a wide bore magnet; preferably, the magnetic field is generated by a room temperature superconducting magnet. While any field strength can be used in the system of the present invention, higher field strengths are preferable to lower field strengths. In one embodiment, magnetic field comprises a 2.01 T magnetic field. The receiver component of the analytical system includes, but is not limited to, preamplifier and a detector in communication with the NMR probe. In one embodiment, the receiver includes a passive rf duplexer and signal mixing and digitization electronics. These and other aspects of the present invention are provided herein.

BRIEF DESCRIPTION OF THE DRAWINGS

FIG. 3 panels A and B represent one embodiment of the systems of the present invention, depicting an experimental setup used to obtain an NMR spectrum of a full, intact wine bottle. FIG. 3A provides a schematic depicting the placement of the sealed consumables container (a wine bottle) and NMR probe within the body structure of an NMR spectrometer. FIG. 3B shows an expanded view of the probe, depicting the positioning of the selected portion of the container with the rf coils of the probe, and indicating that the NMR probe head is capable of housing an entire bottle of wine.

FIG. 4 panels A and B depict an alternative embodiment of the systems of the present invention, showing the placement of the body of the sealed consumables container within the NMR probe. FIG. 4B shows an expanded view of the probe, depicting the positioning of the body of the container within the sample measurement region of the probe.

DETAILED DESCRIPTION

Definitions

Figure 1:
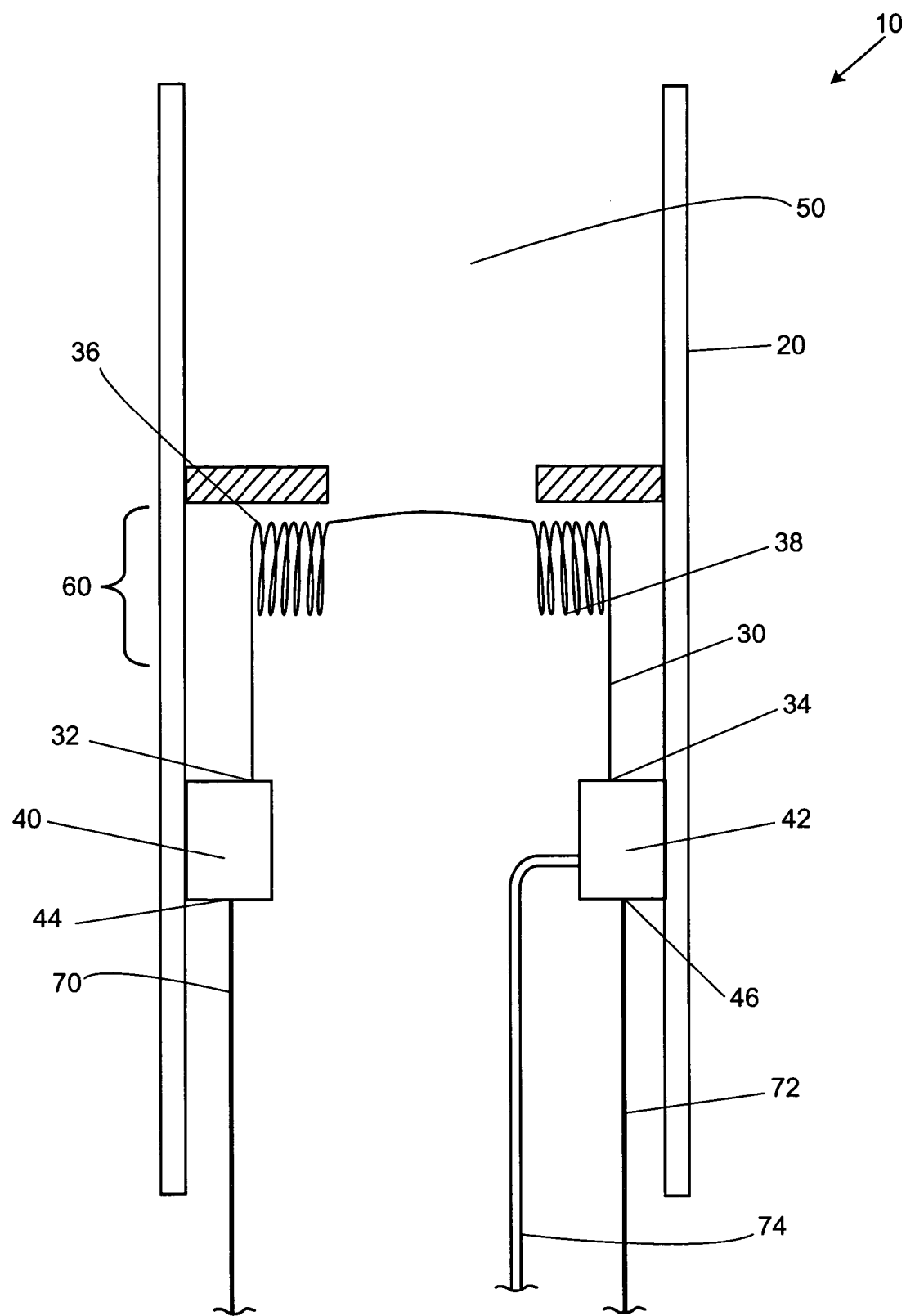
FIG. 1 is a schematic drawing of an exemplary probe of the present invention.

Before describing the present invention in detail, it is to be understood that this invention is not limited to particular devices or container systems, which can, of course, vary. It is also to be understood that the terminology used herein is for the purpose of describing particular embodiments only, and is not intended to be limiting. As used in this specification and the appended claims, the singular forms "a", "an" and "the" include plural referents unless the content clearly dictates otherwise. Thus, for example, reference to "a capacitor" includes a combination of two or more capacitors; reference to a "coil" includes mixtures or series of coils, and the like.

Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein. In describing and claiming the present invention, the following terminology will be used in accordance with the definitions set out below.

The term "consumables" as used herein refers to a food, beverage, or alternate energy source (e.g., bacterial media) intended for consumption by an organism (e.g., a human, an animal, a cell culture, and the like). Thus, the term "sealed consumables container" refers to a packaged or unopened vessel or receptacle containing the food or beverage. Sealed NMR tubes prepared with samples of food or beverage products are not considered sealed consumables containers with respect to the present invention.

The terms "NMR probe" and "probe head" are used interchangeably herein to refer to the component of an NMR spectrometer system which transmits pulses to the sample and receives the NMR signals generated.

The term "data collection region" refers to the portion of the NMR probe in which the NMR signal is generated; typically, the homogeneity of the magnetic field of the spectrometer is optimized in this region.

The term "rf coil" refers to a set of filamentary wire sections arranged in a helical geometry and designed for transmitting and/or receiving radiofrequency signals.

The term "tuning capacitor" as used herein refers to one or more capacitor components of the NMR probe which are typically used to match and tune the probe to the correct Larmor frequency and impedance match the rf circuit to, for example, 50 Ω.

The term "split solenoid coil" (or "split pair solenoid") refers to a solenoid having multiple coils of wire (usually in cylindrical form) that generates a magnetic field when carrying a current.

Methods

The present invention provides methods of analyzing one or more contents of a sealed consumables container. The sealed consumables container can be any of a number of food or beverage containers having contents of interest, including, but not limited to, alcoholic or nonalcoholic beverages.

In a preferred embodiment, the container is a corked (e.g., unopened) bottle of wine. Any number of wine bottle "styles" can be accommodated in the methods (as well as devices and systems) of the present invention. For example, the methods of the present invention can be used to analyzed the contents of the high shouldered "Bordeaux" bottle (typically used for Sauvignon Blanc, Cabernet Sauvignon, Merlot, and Bordeaux blends), the slope shouldered "Burgundy" bottle (Chardonnay and Pinot Noir), or the taller "Hoch" bottle of Germanic origin (Rieslings and Gewuürztraminers). The contents of champagne/sparkling wine bottles, Chianti bottles, and the shaped-neck bottles typically used for fortified wines (port, sherry, etc.) can also be analyzed by the methods of the present invention. Furthermore, a range of bottle sizes can be used in the methods of the present invention; in addition to the 750 mL bottle found in typical wine cellars, the smaller half bottles, "splits" (187 mL) and "tenths" (375 mL) as well as the larger "magnum" bottles (e.g., 1 L, 1.5 L and 3 L bottles) can be examined.

The bottle can be made of either clear or colored (e.g., amber, green or brown) glass. In addition, the beeswax seal and/or lead cap often used in the corking process need not be removed for the analysis.

In addition to wine, other consumables can be analyzed by the methods of the present invention, including, but not limited to, beer, vinegar and olive oil. In addition, sealed receptacles containing solutions or suspensions not typically considered as "food" (e.g., microbial culture media, herbal tinctures, and the like) can also be examined using the methods of the present invention. Preferably, the component of interest in the sealed container generates an NMR spectrum having at one or more sharply defined peaks.

The methods of analyzing one or more contents of the sealed consumables container employ an NMR spectrometer and an NMR probe configured to accept a portion of the sealed consumables container. In one embodiment of the present invention, the NMR probe is configured to receive the narrowed upper portion, or "neck," of the sealed container. In an alternate embodiment, the body of the container is the portion placed in the NMR probe.

In the methods of the present invention, the selected portion of the sealed consumables container is positioned within the data collection region of the NMR probe. This can be achieve by placing the container within the probe, and then inserting the probe into the spectrometer, such that the selected portion of the container (neck, body, etc.) is optimally positioned within the magnetic field of the spectrometer. Alternatively, the probe can be installed into the spectrometer prior to insertion of the container. In either case, the container is positioned such that a portion of the consumables is positioned within the magnetic field of the spectrometer, and proximal to the rf coil of the NMR probe. The examined portion of the sealed container will be determined in part by the shape and/or configuration of the sealed container, as well as various requirements with respect to the type of NMR spectroscopy performed. For example, either the neck of the container or a portion of the body of the container can be placed within the data collection region of the NMR probe.

In one preferred embodiment, the rf coil "examines" the neck of a wine bottle between the base of the cork and the flared body of the wine bottle. Although there is less sample in this region (and therefore less signal) as compared to the larger body of the bottle, it is easier to establish a homogeneous static magnetic field over this smaller sample region, thus enhancing the probability of obtaining narrow (resolved) NMR spectral peaks.

A homogeneous static magnetic field is established across the data collection region of the NMR probe by standard mechanisms, e.g., by adjustment of cryogenic and/or room temperature (RT) magnetic field shims. The NMR spectrum is then collected by monitoring the response of the sample to an rf electromagnetic field pulse generated by the rf coil. Preferably, the magnetic field established is homogeneous enough to allow for resolution of chemical shift differences between selected NMR spectra peaks set a minimum distance apart. The degree of homogeneity necessary for performing the methods of the present invention will depend on a number of factors, including nuclei selection, magnetic field strength, and chemical structure. In the methods of the present invention, the homogeneous static magnetic field is established such that one or more peaks of interest from the contaminant are resolved from additional NMR spectral peaks. For example, for $^1$H NMR spectra collected on the contents of sealed wine bottles, the minimum desired resolution is approximately 1 ppm, the distance between the methyl resonance and the methylene resonance of the acetic acid contaminant. Exemplary NMR spectra of a number of compounds can be found, for example, in the *Aldrich Library of $^1$H and $^{13}$C FT NMR Spectra,* Edition 1 (1993, volumes 1-3, eds. Pouchert and Behnke, Aldrich Chemical Company), from which a desired minimum resolution can be readily determined by one of skill in the art.

Since the magnetic field is not stabilized with a flux-locked loop, and a $^2$H lock (as typically employed with small volume NMR samples "spiked" with a deuterated standard such as TMS) is not possible for sealed wine bottles, data collection is typically performed via block averaging (e.g., n data sets of free induction decay each derived from m scans). In a preferred embodiment, the data are collected as block averages of n=10 groups of 100 scans. The n=10 free induction signals are Fourier transformed, overlapped by shifting the frequency, and added offline using Matlab (Mathworks Inc, Natick Mass.). This procedure eliminates the effect of the long time drift in the static magnetic field on the collected data, thereby producing highly resolved $^1$H NMR spectra for the methyl group region in wine.

After an NMR spectrum is collected, the peaks of the spectrum are examined. Typically, the analysis involves examination of previously-identified peaks in a select region of the spectrum. The peaks can represent any of a number of components found in the sealed container. For example, the peaks of interest are optionally generated by contaminating molecular species (contaminants) indicating spoilage or exposure to oxygen. For embodiments involving the analysis of wine, one particular contaminant of interest is acetic acid, which is generated by the bacterial metabolism of ethyl alcohol. For analysis of acetic acid, the regions of interest are around 1 ppm (the region in which the methyl peak for acetic acid can be found) as well as around 3.6 ppm (the region in which the methylene peak from acetic acid is located). Alternatively, wine components such as aldehydes or flavenoids can be examined.

In some embodiments of the method, the analysis is on a qualitative level, e.g., are the NMR peaks of interest present or absent. In other embodiments, the analysis is quantitative; the selected peaks are integrated and compared to a standard peak intensity, thereby providing a quantitative analysis of the selected components of the sealed consumables container. Preferably, the NMR resonances generated by the component of interest are sharp, facilitating the optional integration process. The integration can be performed using a software program provided with the spectrometer operational software, or it can be performed the old-fashioned way, by printing the spectra, cutting out the peaks of interest, and weighing the paper scraps.

NMR Probes

The present invention also provides NMR probes for use in the methods described herein. The NMR probes of the present invention are configured to position a portion of a sealed consumables container within an NMR spectrometer, thus avoiding the need to violate the seal on the container in order to analyze the contents. The probes typically comprise a body structure having a cavity disposed at a first end of the body structure, a first rf coil positioned proximal to the cavity and the portion of the sealed container; and a tuning capacitor coupled to the rf coil and to a length of coaxial cable configured for connection to the NMR spectrometer. In an alternate embodiment, the cavity is disposed in a middle region of the body structure, rather than proximal to the end of the probe.

The probes of the present invention can be used to detect any desired nuclei capable of generating a nuclear magnetic resonance and having adequate chemical shift dispersion between selected contaminant and/or sample signals. Thus, the probes of the present invention include, but are not limited to, $^1$H probes, $^2$H probes, $^{13}$C probes, $^{17}$O probes, and the like. Furthermore, the probes of the present invention can be single frequency or dual frequency probes (e.g., a $^1$H/$^{13}$C probe).

The body of the probe is typically composed of material having a low magnetic susceptibility to reduce and/or prevent distortion of the static magnetic field when the probe is positioned in the spectrometer. Exemplary materials used in the manufacture of the body structure (or portions thereof) include, but are not limited to stainless steel, aluminum, glass, ceramic, and plastics such as Teflon (polytetrafluoroethene), Kel-F (polychlorotrifluoroetene), and PVC (polyvinylchloride).

The body structure has a cavity that is configured to accept a portion of the sealed consumables container, such that a portion of the container is positioned within the data collection region of the probe. Thus, the sample cavity is greater than that typically employed in an probe configured for NMR tubes. The overall dimensions of the probe optionally range from about 600 mm to 800 mm in length, preferably about 700 mm. The outer diameter of the probe ranges in size from 100 mm to 150 mm in diameter, although an outer diameter of up to 310 mm is possible with the current magnet embodiment. The size of the cavity portion of the probe will depend upon the sealed container to be analyzed; for a probe configured to accept a neck portion of a wine bottle (FIG. 3A and 3B), the cavity portion of the probe will typically range from 34 mm to 85 mm in diameter. Larger cavities able to encompass a wider portion of a consumables container, such as the base and body of a wine bottle (e.g., about 100-150 mm in diameter), are also contemplated (see FIGS. 4A and 4B).

The cavity is configured to hold the sealed container in position through the use of, for example, one or more PVC positioning rings. In one embodiment, the cavity extends from one end of the probe to the data collection region, for insertion of the sealed container from the open end. In an alternate embodiment, the cavity is enclosed within the body structure, and accessed by an opening in the side of the body structure.

The first rf coil is positioned in the body structure of the probe, proximal to the cavity (and the selected region of the sealed container inserted therein). Optionally, the first rf coil functions as both the transmitting coil and the receiving coil.

In one embodiment, the first rf coil is a split solenoid coil. An exemplary split solenoid coil is 12 gauge copper wire wound in a 1 cm diameter spiral, the first coil portion having 4 turns of the copper wire, and coupled (via a connecting portion of the wire) to a second coil portion having another 4 turns of copper wire. The first coil portion is positioned on one side of the cavity, while the second coil portion is positioned on an opposite side of the cavity; the connecting wire runs between the two portions without crossing the cavity itself (e.g., along the circumference of the cavity). Preferably, the second coil portioned is aligned along a same axis as the first coil portion.

In another embodiment, the rf coil circumscribes the cavity (e.g., the walls of the body structure defining the cavity act as a former around which the rf coil is wound.) In a further embodiment of the probe, the first rf coil comprises a birdcage-style coil. Such a configuration of coil portions is described in, for example, Hayes et al. (1985) "An efficient, highly homogeneous radiofrequency coil for whole-body NMR imaging at 1.5 T" *J. Magn. Reson.* 63:622-628.

The probes of the present invention also include one or more tuning capacitors. The tuning capacitor is coupled at a first position to the first rf coil, and coupled at a second position to a length of coaxial cable configured for connection to the NMR spectrometer. In one embodiment, the tuning capacitor is a non-magnetic 0-10 picofarad high power rf capacitor.

A schematic representation of the probes of the present invention is shown in FIG. 1. Probe 10 comprises body structure 20, first rf (radiofrequency) coil 30; and tuning capacitors 40 and 42. Body structure 20 has opening or cavity 50 disposed at one end for receiving the sealed consumables container (not shown).

A portion of cavity 50 extends into data collection region 60 of probe 10. First rf coil 30 is attached to capacitor 40 at a first end 32 and attached to capacitor 42 at a second end 34, and is positioned proximal to cavity 50 such that coil portions 36 and 38 are situated to either side of data collection region 60.

Tuning capacitors 40 and 42 are also coupled at second positions 44 and 46 to coaxial cables 70 and 72, which are configured for connection to the NMR spectrometer (not shown). In addition, tuning capacitor 42 is coupled at a third position to rf in/out coaxial cable 74, which provides the radiofrequency signal for NMR spectrum generation.

Figure 2:
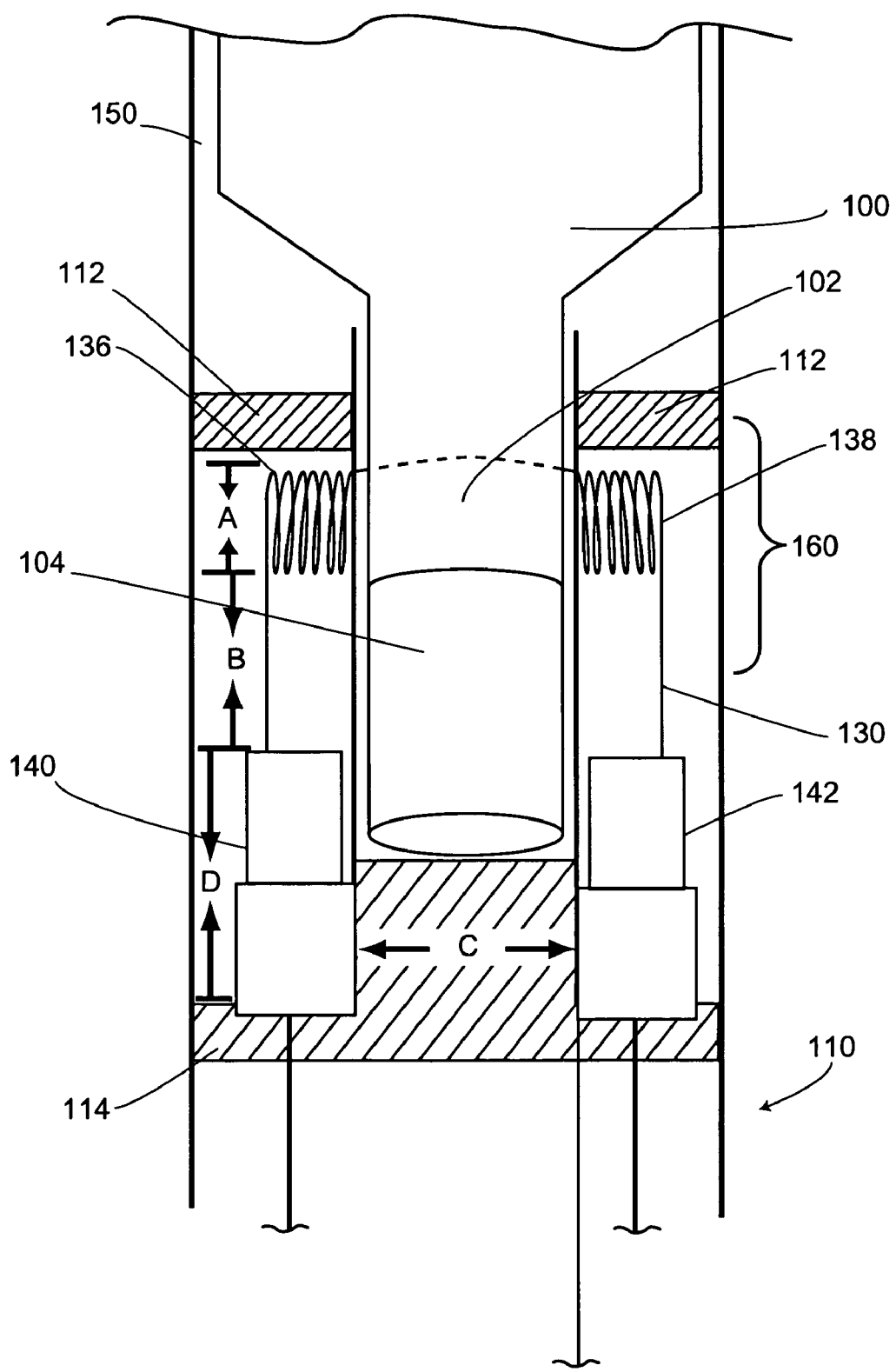
FIG. 2 depicts an expanded view of an exemplary probe, showing the placement of a sealed container within the data collection region.

FIG. 2 depicts an expanded view of exemplary probe 110, showing the placement of sealed container 100 within the data collection region 160. Coil portions 136 and 138 of rf coil 130 are approximately 2.0 cm in diameter (measurement A) and extend approximately 2.5 cm from the upper surface of tuning capacitors 140 and 142, respectively (measurement B), such that the total height of rf coil 130 is approximately 4.5 cm. Coil portions 136 and 138 are positioned approximately 3.4 cm apart (measurement C) with the intermediate coil portion (represented by dotted line) arcing between the two portions, such that neck portion 102 of sealed container 100 can be positioned between coil portions 136 and 138 for optimal data collection. Optionally, container 100 will have stopper 104 positioned at the distal end of neck portion 102. Stopper 104 is optionally a cork, a screw-top cap, or a plug. Preferably, bottle 100 is positioned within data collection region 160 such that stopper 104 does not interfere with the data collection procedure.

Probe 110 optionally includes positioning ring 112 separating rf coil 130 from the main portion of cavity 150; the aperture in positioning ring 112 allows the selected portion of bottle 100 to be positioned within data collection region 160 while protecting this region from dust, etc. Optional capacitor stand 114 is positioned on the distal side of tuning capacitors 140 and 142. Capacitors 140 and 142 are approximately 4.5 cm in height; therefore, the distance between a far edge of coil portion 136 and the distal side of capacitor 140 is approximately 9 cm, and the distance between outer edges of positioning ring 112 and capacitor stand 114 is approximately 11 cm.

The probes of the present invention optionally incorporate a second rf coil, preferably positioned distal to the first rf coil. The second rf coil can be employed for a number of purposes. For example, the second rf coil can be used for either transmitting or receiving the rf signal (in embodiments in which the first rf coil does not function as both transmitter and receiver). Alternatively, the second rf coil can be configured for measurement of one or more signals from a calibration sample. In yet another embodiment, the second rf coil provides for selective excitation of a heteronucleus (including, but not limited to, $^{13}$C, $^{17}$O, $^{2}$H, $^{23}$Na, $^{27}$Al, $^{199}$Hg, $^{207}$Pb, and the like).

Optionally, the probe further includes one or more components for tuning and/or impedance matching the rf coil (s) to at least one rf power source at a selected frequency.

The probes of the present invention optionally include one or more additional components which enhance the functioning of the probe. For example, the probe can include components for generating magnetic field gradients, which can be used, for example, for imaging purposes. In some embodiments, the probe includes a calibration fluid sample tube. The optional calibration sample tube is typically positioned within the cavity of the body structure such that the calibration sample is positioned proximal to the selected portion of the sealed consumables container when the container is inserted in the cavity.

In a further embodiment, the NMR probes of the present invention optionally further include a fluid jacket, reservoir or other mechanism for modulating the temperature of the probe. Exemplary fluid jacket designs for use with the present invention are described in, for example, U.S. Pat. No. 5,530,353 titled "Variable Temperature NMR Probe" (Blanz).

System Components

The present invention also provides systems for analyzing contents of a sealed consumables container. The systems include one or more NMR probes of the present invention, an NMR spectrometer, and a receiver system configured for electronic communication with the NMR probe. The probes and systems of the present invention can be used to perform pulsed, continuous wave, or gradient NMR experiments.

The NMR spectrometer typically comprises a body structure, a magnet housed within the body structure, a bore proximal to the magnet and configured to receive the NMR probe, and an amplifier configured for coupling to a first position on the NMR probe. Optionally, the magnet is a constant external magnet, a room temperature (RT) magnet, and/or a superconducting magnet. Any NMR spectrometer having a bore capable of receiving the NMR probes can be used in the systems of the present invention. Preferably, the NMR spectrometer is a super wide bore spectrometer. Exemplary spectrometers are available commercially from, for example, Varian (Palo Alto, Calif.; www.varianinc.com) and Bruker (Germany, www.bruker.com). The field strength of the magnet component used in the systems can also vary, ranging from 2.01 T to 9.4 T and higher.

The systems of the present invention include a receiver system configured for electronic communication with the NMR probe. Optionally, the receiver system is incorporated into the body structure of the NMR spectrometer. The receiver system typically comprises a preamplifier configured for coupling to the NMR probe and a detector in communication with the preamplifier. In one embodiment of the systems of the present invention, the receiver includes a passive rf duplexer as well as electronics for signal mixing and digitization (see, for example, Fukushima and Roeder, *Experimental Pulse NMR a Nuts and Bolts Approach*, Addison-Wesley, New York, 1981).

Optionally, the system further includes an NMR pulse programmer. Exemplary pulse programmers are available from Tecmag, Inc. (Houston, Tex.; www.tecmag.com).

In some embodiments of the present invention, the system includes a mechanism for spinning the sealed container within the NMR probe. Exemplary spinning mechanisms include, but are not limited to air-propelled mechanisms (e.g., air turbines), rotor mechanisms, strap-based mechanisms and the like.

In a preferred embodiment of the present invention, the system also includes a rf power source, for exciting the nuclei within the sealed container.

FIG. 3A provides an exemplary system of the present invention depicting the positioning of bottle 200 within the data collection region 260 of probe 210, which is inserted into magnet 280 of the NMR spectrometer. FIG. 3B shows the alignment of bottle 200 within probe 210 with respect to rf coil 230 and tuning capacitors 240 and 242. Also depicted are optional components positioning ring 212 and capacitor stand 214.

FIGS. 4A and 4B depict an alternate positioning of bottle 300 within the data collection region of probe 310, in which the body of bottle 300 is inserted into data collection region 360. In FIG. 4A, probe 310 is inserted into magnet 380 of the NMR spectrometer. FIG. 4B shows rf coil 330, tuning capacitors 340 and 342, coaxial cables 370 and 372, and rf in/out cable 374, with respect to the alignment of bottle 300 within probe 310. Positioning ring 376 centers the sample inside of rf coil 330, which is mounted on PVC positioning rings 378 and 379.

EXAMPLES

It is understood that the examples and embodiments described herein are for illustrative purposes only and that various modifications or changes in light thereof will be suggested to persons skilled in the art and are to be included within the spirit and purview of this application and scope of the appended claims. Thus, the following examples are offered to illustrate, but not to limit the claimed invention.

The methods, NMR probes and spectrometer systems of the present invention are capable of detecting less then 0.5 g/L amounts of acetic acid in wine. For the analysis of acetic acid content, the acetic acid methyl group hydrogen nuclei and the ethyl alcohol methyl group hydrogen nuclei are examined, which differ in chemical shift by approximately 1 ppm. This method for acetic acid quantitation does not violate the wine bottle, is harmless to the bottle contents, and can be easily extended to the exploration of other vital ingredients and or contaminants in intact wine bottles and other sealed consumable containers.

Example 1

Determination of Acetic Acid Levels in Wine Samples

Standards Preparation

The titration experiments were performed on full bottle acetic acid standards prepared from mixtures of de-ionized water, 200 proof ethyl alcohol obtained from Gold Shield Chemical Co. (Hayward, Calif.), and 99.7% glacial acetic acid purchased from EM Science (Gibbstown, N.J.). The control samples were generated by filling, or "charging" empty wine bottles with 750 mL of 12.5% (v/v) ethyl alcohol in water having a selected concentration of acetic acid (ranging between about 0.5 g/L and about 3.2 g/L). Sodium chloride (Fisher Scientific, Hampton, N.H.) was dissolved in 750 mL water and used as a calibration standard for both shimming the magnetic field for nuclei with low gyromagentic ratio $\gamma$ and for determining the Larmor frequency of the comparatively less sensitive $^{13}C$ nucleus in full bottle wine samples. The tested wines were either purchased from local markets or obtained as gifts from the UC Davis Department of Viticulture and Enology.

Experimental Set-up

The NMR experiments on sealed wine bottles were performed at 2.01 T magnetic fields corresponding to a $^1H$ Larmor frequency of 85.78 MHz respectively. A high field NMR spectrometer (Varian Inc. Inova 400, Palo Alto, Calif.) employing a 9.1 T magnetic field (corresponding to a H Larmor frequency of 399.76 MHz. The ) was used to confirm the acetic acid concentrations measured on the low field instrument, using 500 µL aliquots of the samples.

The single resonance NMR spectrometer delivers rf pulses to a high power amplifier connected to the NMR probe head mounted inside of an Oxford Instruments (Palo Alto, Calif.) 310 mm room temperature bore superconducting solenoid imaging magnet. The full intact wine bottle is housed inside of the NMR probe head as shown in FIG. 3A. The rf coil is proximal to the neck of the wine bottle between the base of the cork and the main body of the wine bottle.

Careful adjustment of the cryogenic and room temperature magnetic field shims was performed to establish a homogeneous field over the wine bottle (as indicated by a $^1H$ line width of $\leq 4$ Hz). Although there is less sample in this region of the bottle in comparison to the bottle body and base, it is much easier to establish a homogeneous static magnetic field over the small sample region and ultimately produce narrow, highly resolved NMR lines. Current for the room temperature shims was provided by a General Electric Omega series NMR spectrometer magnetic field shim power supply, modified to output -5 V to +5 V DC on each channel. The supply was controlled by a potentiometer bank obtained from a Varian EM 390 (90 MHz) continuous wave NMR spectrometer.

After termination of the rf pulse, the sample emits a low µV-mV rf signal that is mixed to audio frequencies and digitized by the NMR spectrometer. Fourier transformation of this signal yields the standard NMR spectrum. Substantial improvements in dynamic range can be made by selectively exciting and measuring just the methyl group region of the $^1H$ NMR spectrum between 1 and 2.5 ppm. Operation in this way removes the massive background signal from water at 4.8 ppm.

Several different nuclei including deuterium ($^2H$), oxygen ($^{17}O$), carbon ($^{13}C$), and hydrogen ($^1H$) were considered as possible candidates for determining acetic acid levels in wine. Of these possibilities, the $^1H$ nucleus was chosen due to its superior sensitivity and the 1 ppm chemical shift difference between the spectrum of acetic acid and the spectra of water and ethyl alcohol, the two major constituents of wine.

NMR Data Collection: Control Data

Figure 5A:
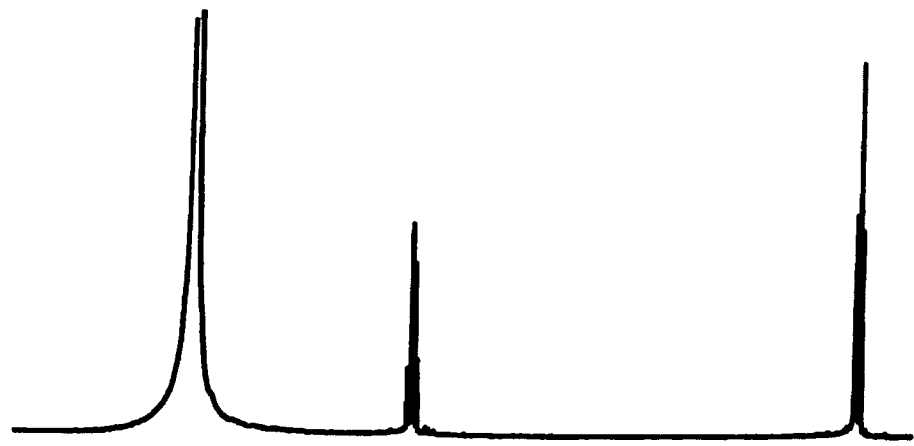
FIG. 5 depicts NMR spectral data obtained at 9.1 T for a 500 μL sample of wine (panel A) and red wine vinegar (panel B).
Figure 5B:

The presence and/or quantity of acetic acid in various wine-based samples was determined by $^1$H NMR spectroscopy at 9.1 T as a control. FIG. 5A provides a portion of an NMR spectrum generated for a 500 µL sample of the 1997 vintage UC Davis Experimental Vineyard Cabernet Sauvignon. The intense peak at 4.8 ppm is due to water, while the quartet and triplet centered at 3.6 ppm and 1.1 ppm represent the methylene and methyl groups in ethyl alcohol, respectively. The $^1$H NMR spectrum in FIG. 5B (also obtained at 9.1 T) corresponds to a homemade sample of red wine vinegar. The new peak at approximately 2 ppm clearly indicates the methyl group in acetic acid, and the lack of splittings of this single line is consistent with the chemical structure. The amount of acetic acid in the red wine vinegar was determined to be 2.6% (or 27.6 g/L), based upon the ratio of the methyl group peak heights in FIG. 5B, assuming that the ethyl alcohol was 12.5% of the full bottle volume prior to acetification.

NMR Data Collection: Experimental Data

Figure 6A:
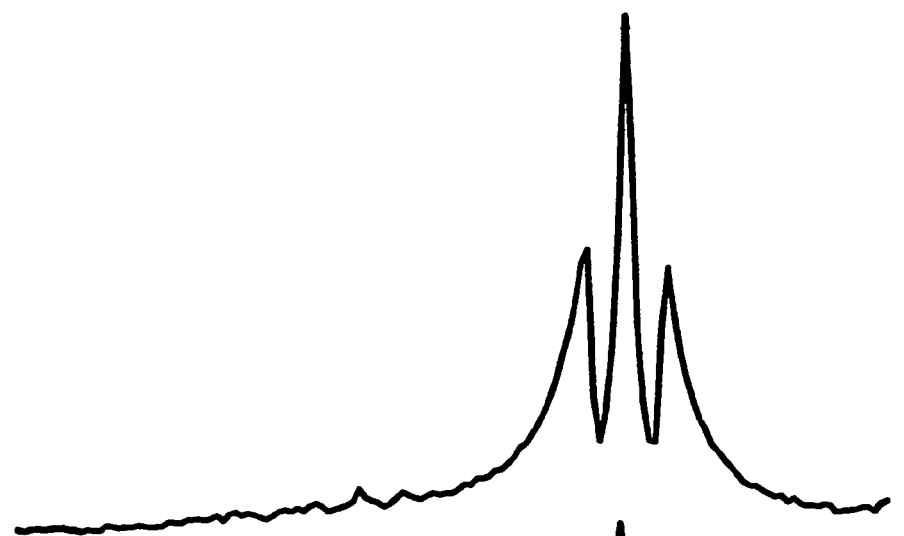
FIG. 6, panels A and B, provides spectral data generated for a sample of wine (panel A) and a sample of red wine vinegar (panel B) using the methods and probes of the present invention.
Figure 6B:
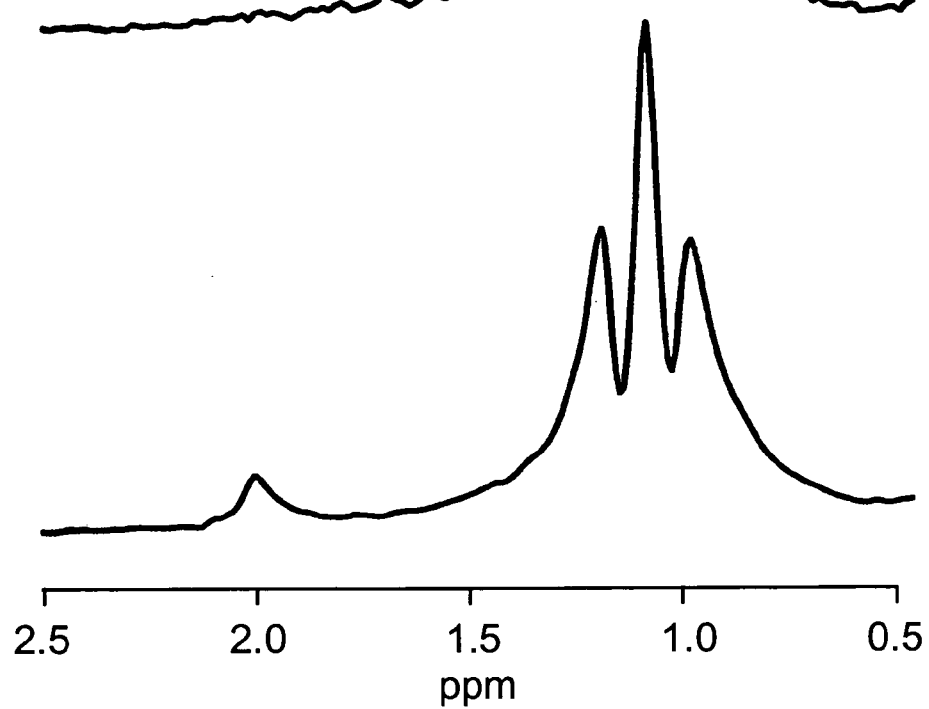

Exemplary data collected by the methods and probes of the present invention is shown in FIGS. 6A and 6B. The $^1$H NMR spectrum in FIG. 6A was obtained for a full bottle of the UC Davis Cabernet Sauvignon, with selective excitation of the methyl group frequencies between ±3 ppm. The triplet-splitting of the methyl resonance depicted in FIG. 6A (corresponding to the triplet shown at 1.1 ppm in the 500 µL sample of FIG. 5A) is due to scalar coupling with the protons in the methylene group in the ethyl alcohol molecule. The full bottle $^1$H NMR spectrum shown in FIG. 6B, corresponds to a 750 mL mixture of water, 12.5% ethyl alcohol, and 0.5% acetic acid. The singlet peak centered at 2.1 ppm (present in the FIG. 6B vinegar sample but not the FIG. 6A wine sample) clearly indicates the presence of acetic acid (as expected) from comparison to the spectrum obtained for the small volume shown in FIG. 5B. The NMR spectrum in FIG. 6B corresponds to an acetic acid concentration of 5.3 g/L, nearly 3.8 times the accepted 1.4 g/L acetic acid spoilage limit for wine.

Titration Data

Figure 7:
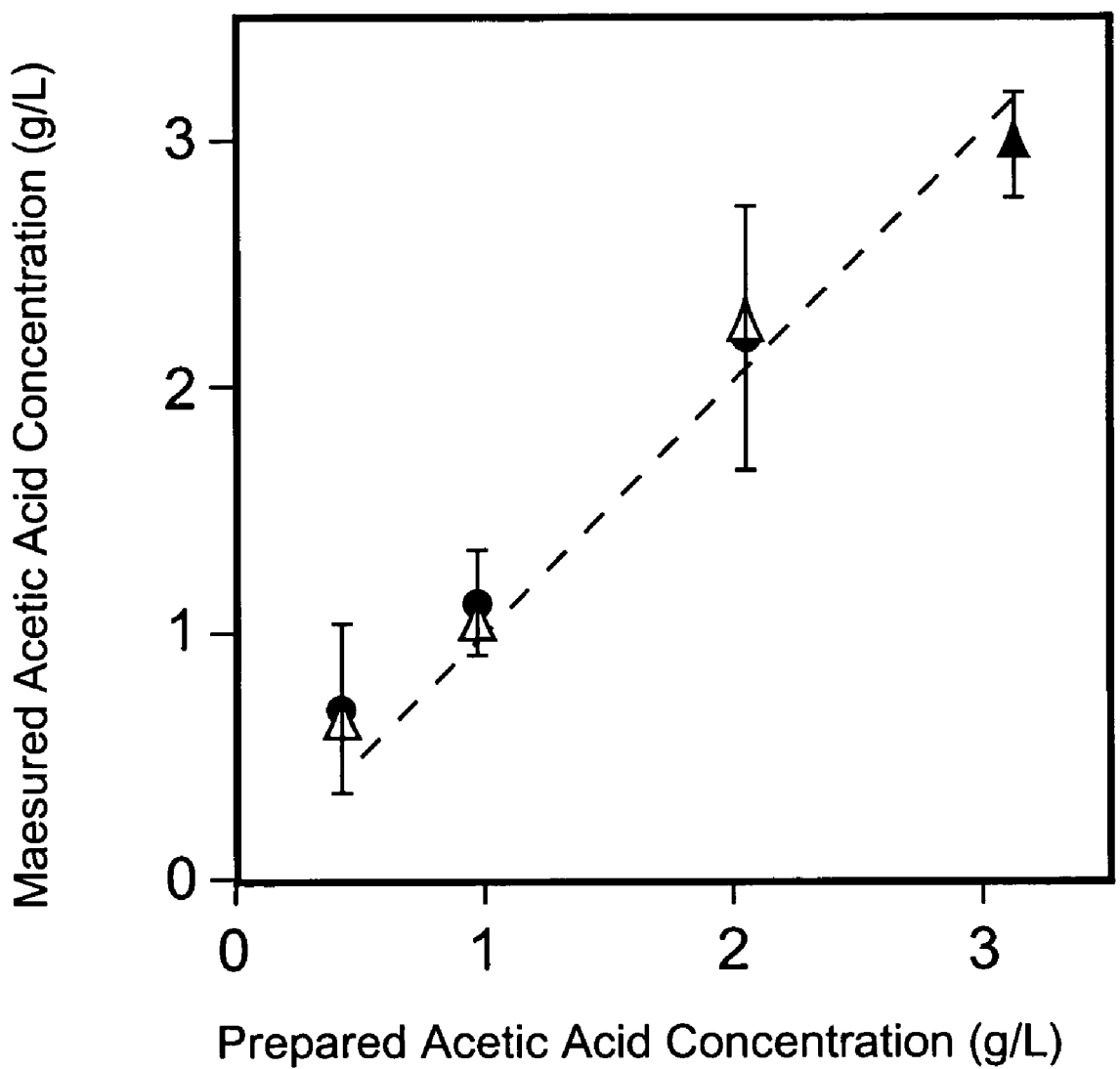
FIG. 7 provides a plot comparing the experimental versus calculated values of acetic acid provided in a set of acetic acid/ethyl alcohol full bottle standard samples.

The titration data shown in FIG. 7 provides a comparison of the prepared acetic acid concentrations versus NMR measurements of acetic acid concentration in the prepared samples, as determined from the ratio of the integrated area of the acetic acid peak at 2.1 ppm to the integrated area of the ethyl alcohol triplet at 1.1 ppm given the 12.5% (v/v) ethyl alcohol concentration. The open circles correspond to the average of nine measurements of the acetic acid concentration from full bottle NMR spectra at 2.01 T, while the open triangles represent one measurement of the acetic acid concentration in a 500 µL sample at 9.1 T. The dashed line of unit slope is included in FIG. 7 indicate the correlation between prepared and experimentally-determined concentrations of acetic acid. Both the low field "full bottle" measurements and the high field "small sample" measurements of acetic acid agree with prepared concentrations, although there is some spread in the data. In the case of the high field small sample results, the uncertainty between the prepared and measured concentrations is most likely due to a liquid volume measurement error in the sample preparation, as the extremely narrow $^1$H NMR line widths as shown in FIG. 5 permit reasonably accurate peak intensity calculation by integration. The increased line widths in the full bottle experiment shown in FIG. 6 introduce more error into the measurement of acetic acid concentration as shown by the error bars in FIG. 7, due to the increased difficulty in assigning starting and ending points for peak integration. Consequently errors in both liquid volume measurements during sample preparation and peak intensity determination introduce slightly deviations from exact agreement with the dashed line in FIG. 7. Improved magnetic field shims yielding narrower lines will substantially increase the accuracy of the acetic acid concentration as measured. However, despite this small disparity, the full bottle method is capable of evaluating the amount of wine acetification down to at least 0.5 g/L, more than half the accepted spoilage limit of 1.4 g/L.

Further Calculations

Figure 8A:
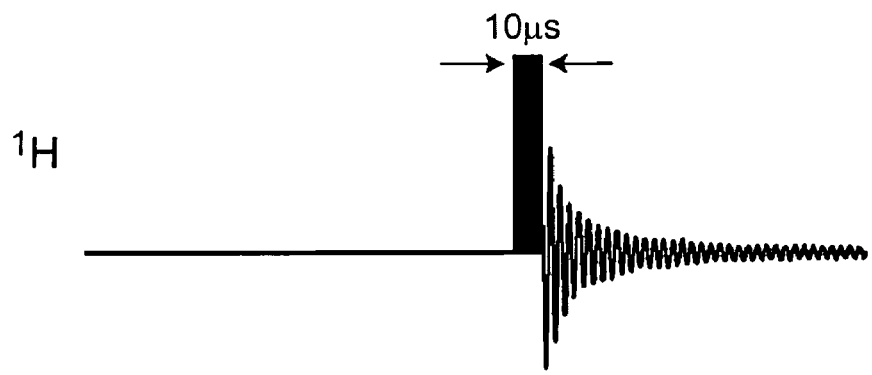
FIG. 8 panels A, B and C provide exemplary rf pulse sequences for use in the methods of the present invention.
Figure 8B:
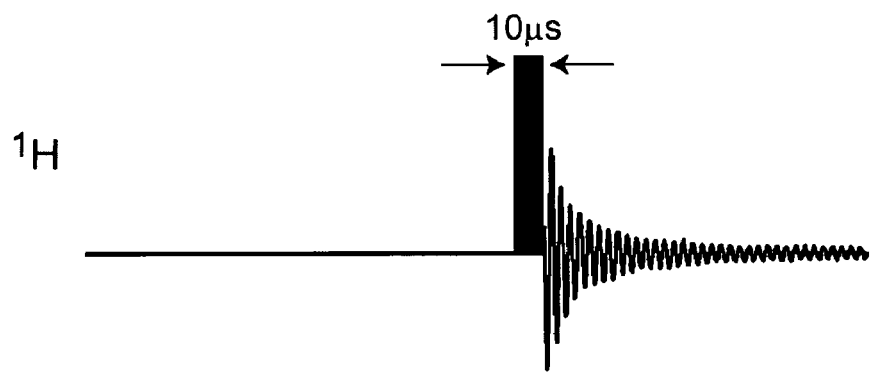

Even though wine is an extremely complex mixture of diverse chemical constituents, a wine sample produces a relatively simple $^1$H NMR spectrum. In the absence of spoilage, the $^1$H NMR spectrum of a sample of wine (as obtained following a single pulse excitation using the sequence provided in FIG. 8A) has a singlet resonance positioned at 4.8 ppm (corresponding to water), as well as an ethanol-derived quartet resonance and triplet resonance centered at 3.6 ppm and 1.1 ppm, respectively. The presence of low levels of acetic acid due to wine spoilage is indicated by another singlet resonance, positioned at 2.1 ppm. Taking the ratio of the integrated intensities of the ethanol triplet to the water peak, and the acetic acid peak to the ethanol triplet allows the percentage of ethanol by volume and the concentration of acetic acid in wine to be quantified as: and $$EtOH\ \%(v/v) = \frac{f_{EtOH} \times 10^3}{(8.5 + 8.2 f_{HOAc}) f_{EtOH} + 4.6}$$

and $$[HOAc](g/L) = \frac{f_{HOAc} f_{EtOH} \times 10^4}{(8.3 + 8.0 f_{HOAc}) f_{EtOH} + 4.5}$$

where the molecular weights and densities of water, ethanol and acetic acid have been used to calculate the values in the denominator of the equations. The measurement of $f_{EtOH}$ is derived from data collected by a one pulse experiment as depicted in FIG. 8A. However, a similar estimate of $f_{HOAc}$ is complicated by the strong water and ethanol signals (e.g., 99% of the spectral intensity). Since the methyl group resonance for ethanol and acetic acid are centered at 1.1 ppm and 2.1 ppm respectively, and that the water resonance is shifted 2.7 ppm downfield from the acetic acid peak (e.g., a 232 Hz downfield shift at 2.01 T), the pulse sequence provided in FIG. 8B can optionally be used for data generation. The combination of selective excitation, delayed acquisition and block averaging can be used reliably and reproducibly to measure $f_{HOAc}$ (see Weekley et al. (March 2003) "Using NMR to study full intact wine bottles" *J. Magn. Reson.* 161:91-98). The 3 ms soft rf pulse "tips" the water magnetization by less than 5 degrees, and when combined with a 200 Hz audio filter bandwidth, the signal intensity of the water peak is attenuated about an order of magnitude. The delayed acquisition combined with the long spin-spin relaxation times for the methyl protons in ethanol and acetic acid reduces the short-lived free induction decay (fid) components that lead to broad spectral lines, thus yielding the desired narrow resonances (e.g., line widths of approx. 4 Hz).

The methyl group region of the $^1$H NMR spectrum for a full bottle of 1997 vintage UC Davis Cabernet Sauvignon is shown in FIG. 6A, while the comparable data for a full bottle having 12.5% (w/v) ethanol dissolved into water, with 0.5% (v/v) added acetic acid is shown in FIG. 6B. The triplets in these spectra correspond to the ethanol methyl group, based upon both the 1.1 ppm chemical shift and the splitting pattern (due to scalar coupling with the two equivalent methylene $^1$H nuclei in the ethanol structure). The single peak at 2.1 ppm in the spectrum shown in FIG. 6B corresponds to acetic acid. Using the formulas provided above, $f_{EtOH}$ is determined to be $6.4 \times 10^{-2}$. The ratio of the integrated intensity of the acetic acid peak to the ethanol triplet in FIG. 6B gives $f_{HOAc}$ as $4.5 \times 10^{-2}$, which can be used to calculate that the concentration of acetic acid [HOAc] in the sample is 5.7 g/L, as compared to the solution as prepared (5.3 g/L of acetic acid in the 0.5% (v/v) standard solution). The 0.4 g/L difference between these measurements is probably due to error in the standard preparation.

Example 2

Determining Acetic Acid Spoilage in Unopened Bottles of Wine

In most practical applications, there is no prior knowledge of the ration $f_{EtOH}$, because wines of different vintages, sources, types and quality can differ in ethanol concentration between about 7% to 24% (v/v). In these situations, the pulse sequence as provided in FIG. 8A is first used to measure the entire $^1$H NMR spectrum, followed by application of the pulse sequence of FIG. 8B to selectively excite and detect the methyl group region. In this manner, both $f_{EtOH}$ and $f_{HOAc}$ can be measured peak integrals and used to calculate the percentage of ethanol and concentration of acetic acid. As noted above, data collection is typically performed via block averaging (e.g., as block averages of n=10 groups of 100 scans. The sets of free induction signals are Fourier transformed, overlapped by shifting the frequency, and added offline. This procedure eliminates the effect of the long time drift in the static magnetic field on the collected data, thereby producing highly resolved $^1$H NMR spectra for the methyl group region in wine, which can be used to accurately measure $f_{HOAc}$.

Figure 10A:
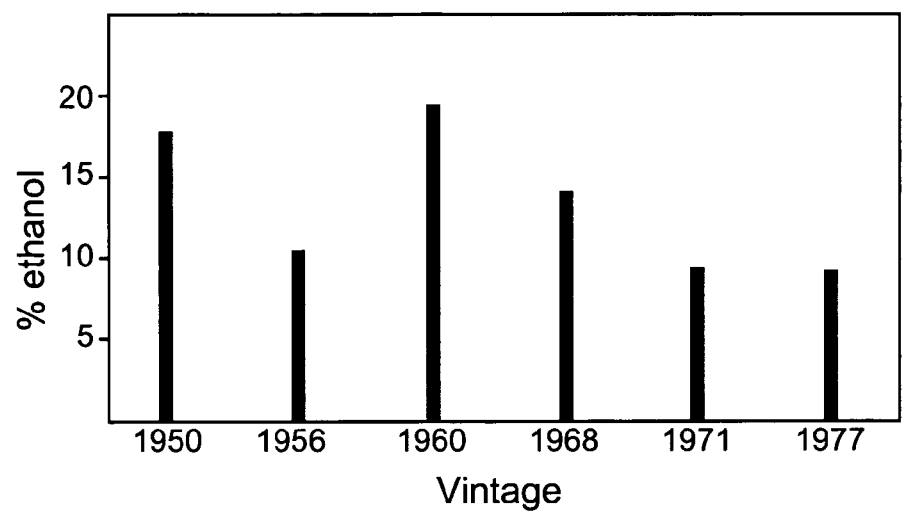
FIG. 10 panels A and B are tables depicting NMR-derived percentages of ethanol (FIG. 10A) and acetic acid concentrations (FIG. 10B) in a vertical series of sealed full bottles of the UC Davis Cabernet Sauvignon bottled between 1950 and 1977.
Figure 10B:
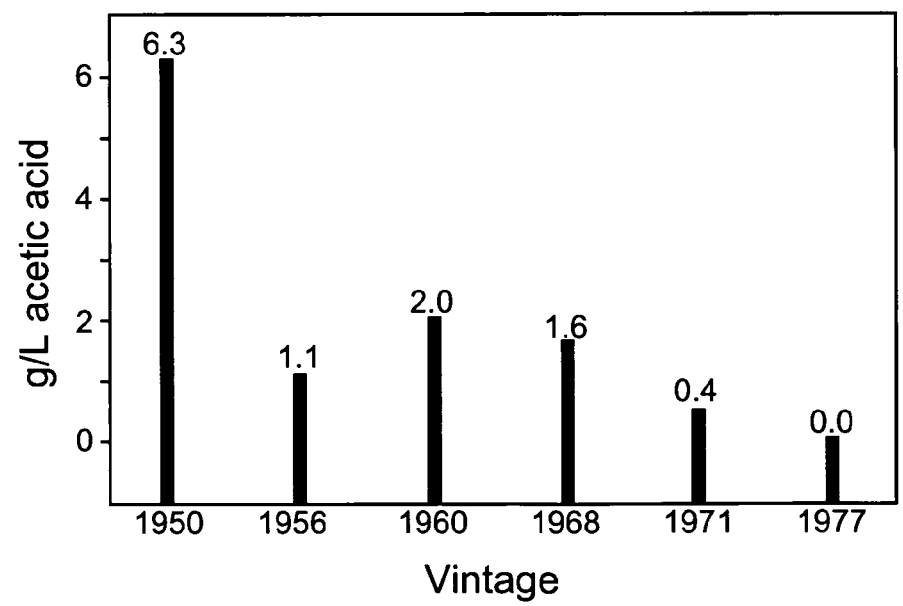

The accuracy and sensitivity of this approach has been tested in full bottles by comparing the NMR-derived concentrations to actual prepared concentrations. The one-to-one agreement between the different concentration measurements with the less than 0.1 g/L acetic acid sensitivity of the full bottle NMR approach prompts further analysis. The NMR-derived percentages of ethanol (FIG. 10A) and acetic acid concentrations (FIG. 10B) in a vertical series of sealed full bottles of the UC Davis Cabernet Sauvignon bottled between 1950 and 1977 were compared. As expected, the amount of ethanol in this series does not correlate well with the year, and varies between 10-20%. Interestingly, the two most recent vintages display concentrations of ethanol very close to the industry standard for most wines (12.5% v/v). A similar lack of correlation is observed (FIG. 10B) for the full bottle acetic acid concentrations for these same wines. Although he oldest wine displays the largest degree of acetic acid spoilage (6.3 g/L), and the youngest wine has no measurable acetic acid contamination, the acid concentration in the other vintages caries between 0.4 g/L and 2.0 g/L. It is therefore incorrect to assume that older wines will automatically have a higher concentration of acetic acid as compared to younger wines. The integrity of the cork (and hence the quality of the bottle seal against oxygen leakage with time) is of paramount importance to acetic acid contamination.

It should be emphasized that the apparatus is capable of investigating a variety of common bottle shapes and sizes, as well as other sealed consumables containers. All of these factors including the effects of lead or metallic seals can be compensated for by carefully adjusting the home built room temperature magnetic field shims. Additionally, the lead or metallic seals do not measurably interfere with the probe tuning or the homogeneity and intensity of the rf field across the wine bottle. Although the titration data shown in FIG. 7 only documents results down to 0.5 g/L acetic acid, levels down to 0.1 g/L have been measured with the probes and systems of the present invention. It is anticipated that NMR solvent suppression techniques and/or a dual coil NMR probe head will extend the sensitivity by one or more orders of magnitude.

Example 3

$^{13}$C NMR Spectroscopy of Full Bottle Samples

As noted herein, the present invention for the NMR analysis of sealed consumables containers are not limited to methods and devices involving performing $^1$H NMR spectroscopy. In an effort to increase the sensitivity of measurements of dilute components (like flavenoids and aldehydes), as well as to extend the full bottle technique to nuclei other than $^1$H, an additional probe embodiment was constructed (see FIGS. 4A and 4B). Instead of examining the approximately 25 cm$^3$ sample volume in the neck of the wine bottle, the probe can be used to analyze the much larger (~1 L) volume in the body of the wine bottle. Although the magnetic field homogeneity is worse across a larger sample volume, examination of nuclei having a larger chemical shift dispersion than $^1$H will be less sensitive to the increased line width.

In one embodiment of the methods of the present invention, sealed consumables containers are examined using $^{13}$C NMR spectroscopy. The much wider chemical shift range and lower Larmor frequency of $^{13}$C as compared to $^1$H (21.56 MHz versus 85.78 MHz at 2.01 T, respectively) reduced the necessity for narrow line width for analysis. As such, it becomes feasible to center the rf detection coil on the main body of the wine bottle, thereby improving sensitivity (due to greater volume of nuclei) without sacrificing the rf coil filling factor.

Figure 8C:
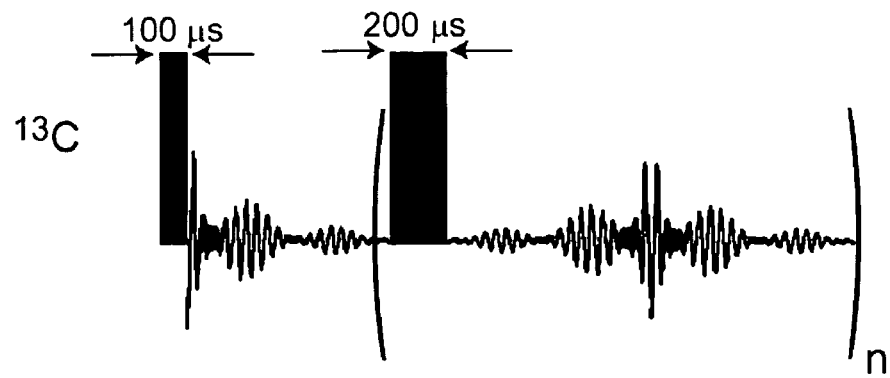
Figure 9A:
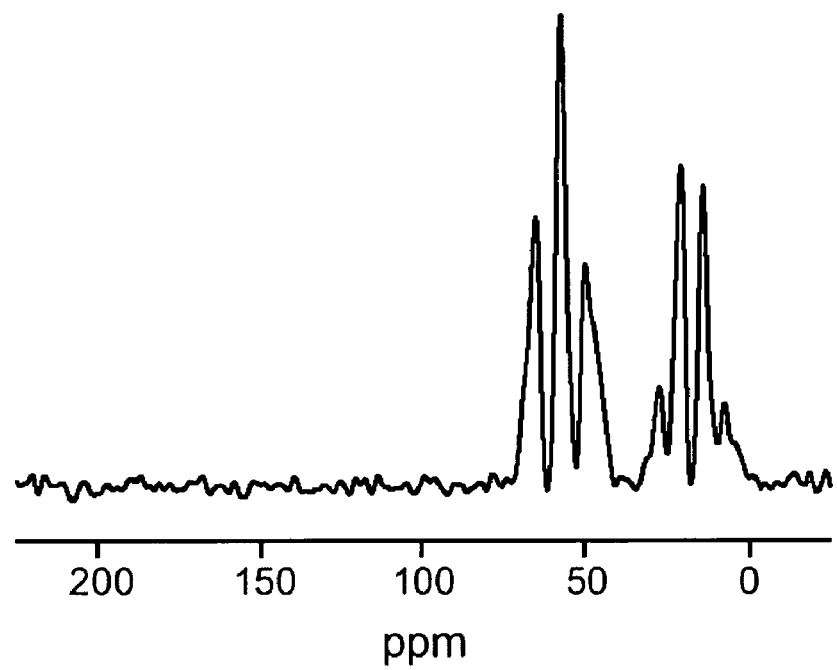
FIG. 9 panels A and B depict $^{13}$C NMR spectra on full bottles of wine.
Figure 9B:
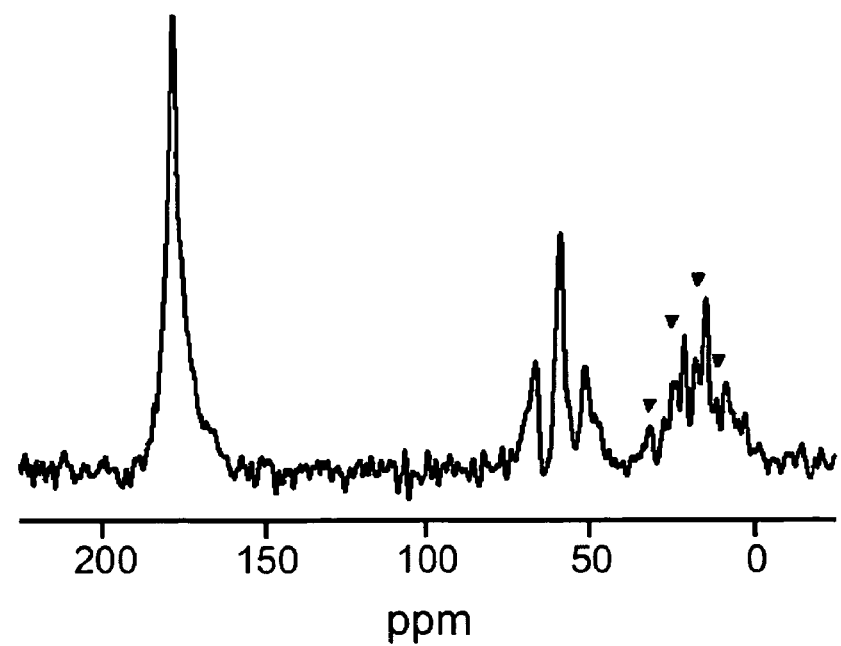

The formation of spin echoes for low γ nuclei is possible using the probes of the present invention (see, for example, FIGS. 4A and 4B), despite the observation that the geometry of the four turn split solenoid rf coil is not optimized for homogeneity. In the special case of $^{13}$C NMR spectroscopy, in which the spin-lattice and spin-spin relaxation times tend to be long, multiple π pulse sequences (as depicted in FIG. 8C) can be employed to refocus the magnetization and increase the signal to noise ratio (S/N) for a fixed number of scans by adding (offline) the free induction signal following the 100 μs π/2 pulse to the echo signals appearing at 102 ms intervals. In this manner, fully $^1$H-coupled $^{13}$C NMR spectra corresponding to 100-1000 scans can be obtained for full bottle samples in a reasonable period of time FIGS. 9A and 9B depict $^{13}$C spectra on full bottles of either the 1997 UC Davis Cabernet Sauvignon (9A) or red wine vinegar (9B), using the pulse sequence provided in FIG. 8C with n=7. The triplet and quartet centered at 57 ppm and 18 ppm arise from the methylene and methyl carbons of ethanol, respectively. The line splitting of about 140 Hz in both of these peaks, as well as their splitting patterns, are consistent with scalar coupling to directly bonded $^1$H nuclei. In the vinegar sample, additional $^{13}$C peaks are seen at 18 ppm and 21 ppm, due to the carbonyl and methyl groups of the acetic acid. The inverted triangles in FIG. 10B label the acetic acid methyl group quartet. The near-equal integrated intensity of the nested quartets suggests that the amount of ethanol and acetic acid in the sample of red wine vinegar are nearly equal, a result consistent with the literature (Jakish (1985) *Modern Winemaking* Cornell University Press, Ithaca N.Y.).

It is clear from the spectra that the full bottle $^{13}$C NMR method is feasible for the exploration of additional wine components, such as tannins, flavenoids, phenols, aldehydes and amino acids. In principle, continues signal averaging will reveal these peaks in the $^{13}$C spectrum, although the spectra will be very complicated in the absence of decoupling from the $^1$H nuclei. Optionally, an additional $^1$H channel is incorporated into the probes of the present invention, thereby providing increased resolution and sensitivity (and potentially, nuclear Overhauser effects) through the use of $^1$H decoupling. Furthermore, probe embodiments for detection of additional isotopes, such as $^{207}$Pb, $^{199}$Hg, $^{45}$Sc, $^{39}$K, $^{27}$Al, $^{23}$Na and the like are also contemplated. Although the abundance of these isotopes is typically below the detection limit for standard (i.e., microliter volume) NMR spectroscopy, the increased volumes employed in the full bottle spectroscopic methods and probes amplifies the number of spins by a factor of $10^4$, thus making the study of trace elements in native wine samples accessible for the first time. Moreover, the methods and devices of the present invention can be used to analyze the quality and nature of the wine bottle itself (e.g., by a combination of $^{29}$Si and $^{23}$Na NMR spectroscopy), while the cork (either natural or synthetic) could be studied, e.g., using $^{13}$C solid state NMR techniques.

The discussion above is generally applicable to the aspects and embodiments of the present invention. Moreover, modifications can be made to the methods, apparatus, and systems described herein without departing from the spirit and scope of the invention as claimed, and the invention can be put to a number of different uses including the following:

The use of an NMR probe configured to accept a sealed consumables container or an NMR system as set for the herein, for performing any of the methods and assays set forth herein.

The use of an NMR probe or system as described herein for performing noninvasive analysis of a corked wine bottle or any other sealed consumables container, e.g., for analysis of one or more contaminants, as set forth herein.

A kit comprising one or more standard solutions of contaminant (e.g., acetic acid titration samples) in a sealed consumables container, for use in the methods, devices or systems of the present invention. Optionally, the kit further comprises an instruction manual for performing the methods of the present invention.

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above can be used in various combinations. All publications, patents, patent applications, and/or other documents cited in this application are incorporated by reference in their entirety for all purposes to the same extent as if each individual publication, patent, patent application, and/or other document were individually indicated to be incorporated by reference for all purposes.

What is claimed is:

1. A method of examining the contents of a sealed container for the presence of one or more components, the method comprising:
   providing an NMR spectrometer and an NMR probe configured to accept a portion of the sealed container, wherein the container is not an NMR tube;
   positioning the portion of the container within a data collection region of the NMR probe;
   collecting NMR data and generating a Fourier-transformed NMR spectrum; and
   examining the NMR spectrum for NMR peaks derived from the one or more components, thereby determining the presence of one or more components in the sealed container.

2. The method of claim 1, wherein the sealed container comprises a consumables container.

3. The method of claim 1, wherein the sealed container comprises a beverage container.

4. The method of claim 1, wherein the one or more components comprise an alcoholic or nonalcoholic liquid.

5. The method of claim 4, wherein the alcoholic or nonalcoholic liquid comprises hydrogen atoms, and wherein the NMR probe comprises a $^1$H NMR probe.

6. The method of claim 1, wherein the component comprises an acid.

7. The method of claim 1, wherein the component comprises an aldehyde.

8. The method of claim 1, wherein positioning the portion of the container comprises placing a neck of the container within the data collection region of the NMR probe.

9. The method of claim 1, wherein positioning the portion of the container comprises placing a body of the container within the data collection region of the NMR probe.

10. The method of claim 1, wherein collecting the NMR data comprises attenuation of a water resonance using a radiofrequency (rf) pulse prior to data collection.

11. The method of claim 1, wherein collecting the NMR data comprises block averaging of data sets.

12. The method of claim 1, wherein examining the NMR spectrum further comprises determining a concentration of the one or more components.

13. The method of claim 1, further comprising:
   establishing a homogeneous static magnetic field across the data collection region prior to collecting the NMR data.

14. An NMR probe configured to position a portion of a sealed container other than an NMR tube within an NMR spectrometer, the probe comprising:
   a body structure having a cavity disposed at a first end of the body structure, said cavity being adapted for receiving a portion of the sealed container;
   a first rf coil positioned proximal to the cavity and the portion of the sealed container; and,
   a tuning capacitor coupled at a first position to the rf coil and coupled at a second position to a length of coaxial cable configured for connection to the NMR spectrometer;
   wherein the probe comprises a $^1$H probe, a $^2$H probe, a $^{13}$C probe, an $^{17}$O probe, a $^{23}$Na probe, a $^{27}$Al, a $^{199}$Hg, or $^{207}$Pb probe.

15. The NMR probe of claim 14, wherein the sealed container comprises a consumables container.

16. The NMR probe of claim 14, wherein the sealed container comprises a beverage container.

17. The NMR probe of claim 14, wherein the first rf coil comprises a coil used for both transmitting and receiving rf pulses.

18. The NMR probe of claim 14, further comprising a second if coil positioned distal to the first rf coil.

19. The NMR probe of claim 18, wherein the second rf coil is configured for measurement of one or more signals from a calibration sample.

20. The NMR probe of claim 18, wherein the second rf coil is configured for selective excitation of a heteronucleus.

21. The NMR probe of claim 20, wherein the heteronucleus comprises $^{13}C$, $^{17}O$, $^{2}H$, $^{23}Na$, $^{27}Al$, $^{199}Hg$, or $^{207}Pb$.

22. The NMR probe of claim 14, further comprising components for generating one or more magnetic field gradients, wherein the components are coupled to the body structure.

23. The NMR probe of claim 22, wherein the components for generating one or more magnetic field gradients comprise imaging components.

24. A system for examining the contents of a sealed container other than an NMR tube, comprising:
    the NMR probe of claim 14;
    an NMR spectrometer comprising a body structure, a magnet housed within the body structure, a bore proximal to the magnet and configured to receive the NMR probe, thereby positioning a portion of the container within a magnetic field generated by the magnet, and an amplifier configured for coupling to a first position on the NMR probe; and,
    a receiver system configured for electronic communication with the NMR probe, the receiver system comprising a preamplifier configured for coupling to a second position on the NMR probe and a detector in communication with the preamplifier.

25. The system of claim 24, wherein the magnet comprises a room temperature superconducting magnet.

26. The system of claim 24, further comprising an NMR pulse programmer.

* * * * *